US012653392B2

(12) United States Patent
Sokoya

(10) Patent No.: US 12,653,392 B2
(45) Date of Patent: Jun. 16, 2026

(54) AUDIOVISUAL TELECONFERENCING WITH IMAGE DATA CAPTURED BY A MEDICAL SCOPE

(71) Applicant: SCOPEREMOTE, LLC, Atlanta, GA (US)

(72) Inventor: Fiyin Sokoya, Atlanta, GA (US)

(73) Assignee: SCOPEREMOTE, INC, Atlanta, GA (US)

( * ) Notice: Subject to any disclaimer, the term of this patent is extended or adjusted under 35 U.S.C. 154(b) by 610 days.

(21) Appl. No.: 18/147,533

(22) Filed: Dec. 28, 2022

(65) Prior Publication Data

US 2024/0215812 A1 Jul. 4, 2024

(51) Int. Cl.
| | |
|---|---|
| *A61B 1/227* | (2006.01) |
| *A61B 1/005* | (2006.01) |
| *A61B 1/05* | (2006.01) |
| *A61B 1/07* | (2006.01) |
| *A61B 1/233* | (2006.01) |
| *A61B 1/267* | (2006.01) |
| *H04N 7/15* | (2006.01) |
| *H04N 9/73* | (2023.01) |

(52) U.S. Cl.
CPC .............. *A61B 1/227* (2013.01); *A61B 1/005* (2013.01); *A61B 1/05* (2013.01); *A61B 1/07* (2013.01); *A61B 1/233* (2013.01); *A61B 1/267* (2013.01); *H04N 7/15* (2013.01); *H04N 9/73* (2013.01)

(58) Field of Classification Search
None
See application file for complete search history.

(56) References Cited

U.S. PATENT DOCUMENTS

| | | | | |
|---|---|---|---|---|
| 10,390,718 B2* | 8/2019 | Chen | .................... | A61B 1/3132 |
| 2009/0284649 A1* | 11/2009 | Pease | ................. | G02B 23/2476 |
| | | | | 348/376 |
| 2015/0065803 A1* | 3/2015 | Douglas | ................. | G06T 7/143 |
| | | | | 600/200 |
| 2015/0173598 A1* | 6/2015 | Alexander | ......... | A61B 1/00154 |
| | | | | 600/187 |
| 2017/0020382 A1* | 1/2017 | Sezan | .................. | A61B 1/0627 |
| 2018/0192965 A1* | 7/2018 | Rose | .................... | A61B 5/0002 |
| 2019/0246884 A1* | 8/2019 | Lu | ....................... | G02B 23/2484 |
| 2021/0068646 A1* | 3/2021 | Zhang | ................ | A61B 1/0684 |
| 2021/0330189 A1* | 10/2021 | Rose | .................... | H04W 12/03 |
| 2022/0265350 A1* | 8/2022 | Clayman | .............. | A61B 1/2736 |
| 2022/0378400 A1* | 12/2022 | Yu | ........................ | A61B 8/5215 |
| 2023/0172427 A1* | 6/2023 | Clark | .................... | G16H 50/20 |
| | | | | 600/109 |
| 2024/0148400 A1* | 5/2024 | Orphanos | .......... | A61B 1/00135 |
| 2024/0215812 A1* | 7/2024 | Sokoya | ................. | G16H 80/00 |
| 2024/0366079 A1* | 11/2024 | Mock | ...................... | A61B 1/24 |

* cited by examiner

*Primary Examiner* — Daniel T Tekle
(74) *Attorney, Agent, or Firm* — TechLaw Ventures, PLLC; Terrence J. Edwards

(57) ABSTRACT

Audiovisual teleconferencing providing image data captured by a medical scope. A system includes a scope comprising an image sensor and a processor in electronic communication with the image sensor. The processor is configured to execute instructions including receiving an image output by the image sensor and providing the image to a remote server by way of a network connection. The remote server communicates the image to each of a first computing device and a second computing device in near real-time.

20 Claims, 12 Drawing Sheets

300

302

109

106

102

500

120

114                    116                    118

600

121

117                    119

700

900

```
┌──────────────────┐  ┌──────────────────┐  ┌──────────────────┐
│ Nasal Cavity     │  │ External Auditory│  │ Oral Cavity      │
│ Camera           │  │ Canal Camera     │  │ Camera           │
│ 902              │  │ 904              │  │ 906              │
└──────────────────┘  └──────────────────┘  └──────────────────┘
```

Image Processing
908

Communication To Patient's Phone
910

Remote Imaging Application
912

Establishing A Network Connection Between A First Computing Device And A Second Computing Device.
1002

Receiving A Video Stream Captured By A Scope In Communication With The First Computing Device.
1004

Providing The Video Stream To Each Of The First Computing Device And The Second Computing Device In Near Real-Time.
1006

AUDIOVISUAL TELECONFERENCING WITH IMAGE DATA CAPTURED BY A MEDICAL SCOPE

TECHNICAL FIELD

The disclosure relates generally to visualization systems and specifically relates to systems and methods for remote processing and analysis of image frames and video streams.

BACKGROUND

Healthcare visits are traditionally performed in-person and require the patient to visit a healthcare professional at a clinic, hospital, or other facility to receive care. However, there are numerous disadvantages to in-person healthcare visits. One significant disadvantage is that many patients who need care are currently ill and may be contagious or feel too unwell to travel and wait to see a healthcare professional. Additionally, in-person visits can be challenging for patients who live in remote areas or patients who wish to consult with specialists that live far away. Further, patients who are out of town on business or vacation may desire to consult with the same physician they are accustomed to even when they are not at home. Technological advancements enable people to share information and to speak and video conference with one another in real-time. It is desirable that the healthcare field leverage these advancements in technology to enable patients to remotely visit with healthcare professionals.

One specialty in healthcare that continues to offer in-person visits is the field of otolaryngology, or the medical specialty that deals with disorders and conditions of the ear, nose, and throat (ENT) region. ENT specialists typically meet with patients in-person to visualize the patient's external auditory canal, nasal cavity, and oral cavity to identify issues and diagnose the patient's condition. This can be inconvenient for patients and may promote the spread of disease if the patient is currently ill and contagious. Therefore, it is desirable to enable patients to remotely consult with ENT specialists and provide the ENT specialists with visualization into the patient's external auditory canal, nasal cavity, and oral cavity.

In light of the foregoing, disclosed herein are systems, methods, and devices for remote visualization and image processing.

BRIEF DESCRIPTION OF THE DRAWINGS

Non-limiting and non-exhaustive implementations of the present disclosure are described with reference to the following figures, wherein like reference numerals refer to like parts throughout the various views unless otherwise specified. Advantages of the present disclosure will become better understood with regard to the following description and accompanying drawings where.

DETAILED DESCRIPTION

Disclosed herein are systems, methods, and devices for remote visualization and image processing. Specifically disclosed herein are means for audiovisual teleconferencing with image data captured by a medical scope. The systems, methods, and devices described herein enable a medical practitioner to review a video stream captured with a medical scope in near real-time, even if the medical practitioner is located in a remote location and cannot personally capture the video stream. The video stream may be captured by a patient, patient assistant, or other medical professional, and then reviewed by a specialist located in a remote location.

Disclosed herein is a visualization system for capturing imaging data of a patient's ear, nose, and throat (ENT) regions. The imaging data captured by the visualization device can be provided to an ENT specialist or imaging technician in real-time by way of a network connection. The visualization systems described herein enable ENT patients to remotely visit with ENT physicians, and provide real-time imaging data of the patient's ear, nose, or throat regions without an in-person visit.

Before the structures, systems, and methods for remote visualization and imaging processing are disclosed and described, it is to be understood that this disclosure is not limited to the particular structures, configurations, process steps, and materials disclosed herein as such structures, configurations, process steps, and materials may vary somewhat. It is also to be understood that the terminology employed herein is used for the purpose of describing particular embodiments only and is not intended to be limiting since the scope of the disclosure will be limited only by the appended claims and equivalents thereof.

In describing and claiming the subject matter of the disclosure, the following terminology will be used in accordance with the definitions set out below.

It must be noted that, as used in this specification and the appended claims, the singular forms "a," "an," and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps.

As used herein, the phrase "consisting of" and grammatical equivalents thereof exclude any element or step not specified in the claim.

As used herein, the phrase "consisting essentially of" and grammatical equivalents thereof limit the scope of a claim to the specified materials or steps and those that do not materially affect the basic and novel characteristic or characteristics of the claimed disclosure.

Figure 1:
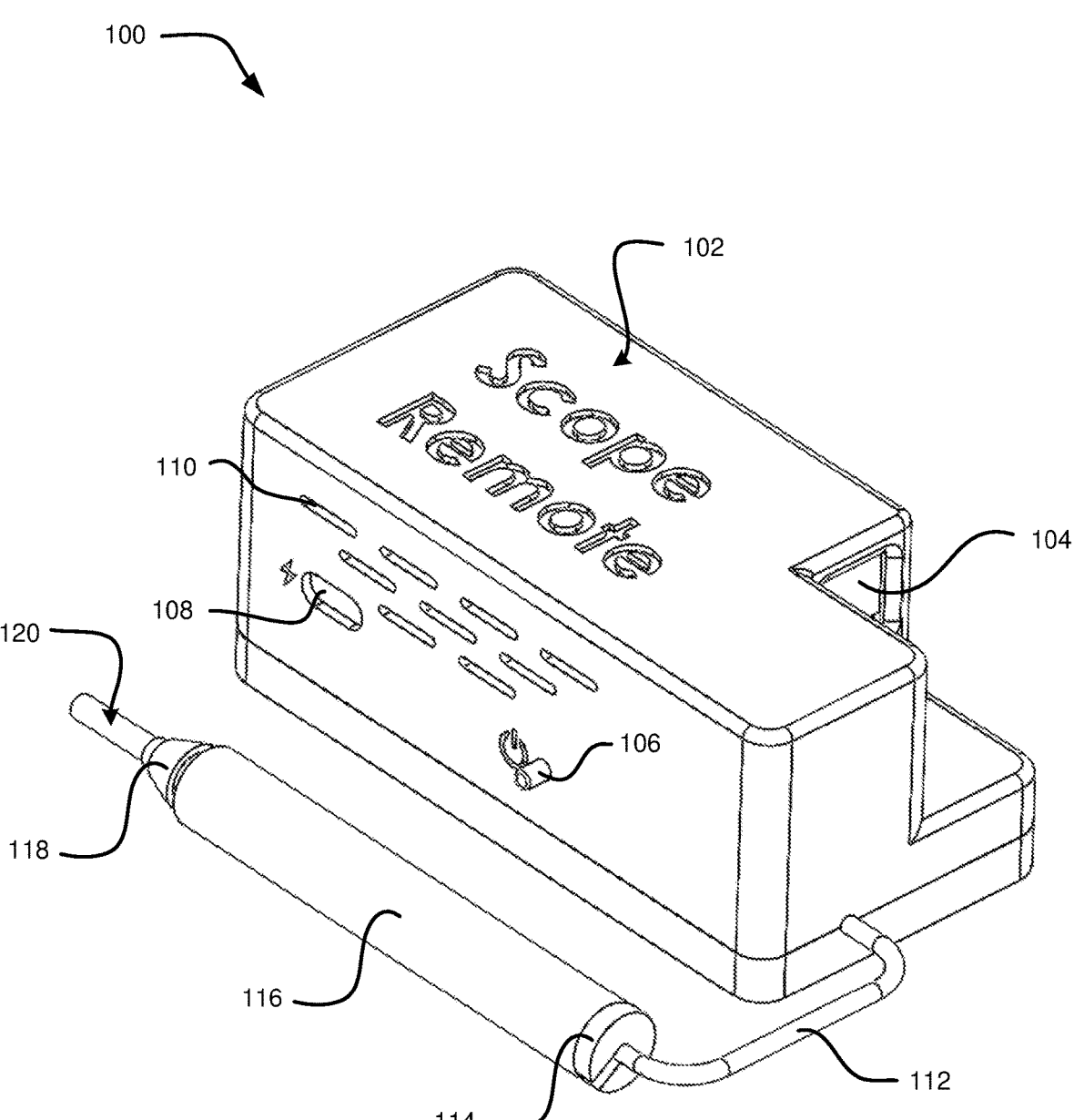
FIG. 1 is a perspective view of a system for remote visualization of a patient's ear, nose, or throat regions.

Referring now to the figures, FIG. 1 illustrates a perspective view of a system 100 for remote visualization of a patient's ear, nose, or throat regions. The system 100 may specifically be implemented to visualize interior regions of the patient's body, including the patient's nasal passage, pharynx, larynx, nasopharynx, oropharynx, ear labyrinth, and so forth.

The system 100 includes a housing 102 for holding electrical components and providing walls to support the various imaging components and connections disposed therein. The housing 102 includes port accessibility regions, including, for example, a region providing access to a network port 104 wherein the system 100 may be hardwired to the Internet by way of an Ethernet® or similar connection. The housing 102 includes a power switch 106 (or an opening whereby a power switch 106 may pass through the housing 102) for turning the system 100 on and off. The housing 102 includes a data port opening 108 providing a means to form a direct electrical connection with components disposed within the housing 102. The data port opening 108 may include a hole disposed through a wall of the housing 102 enabling a cable to pass through and interact with a corresponding data port attached to the electrical components within the housing 102. The housing 102 includes one or more vents 110 for venting electrical components disposed within the housing.

The system 100 includes a cable 112 providing electrical communication between components stored within the housing 102 and imaging components disposed within a handpiece unit. The handpiece unit includes a handpiece housing 116 and a tip 120. The tip 120 may be selected for different imaging purposes, e.g., the tip 120 may be optimized for visualization of a patient's ear, nose, or throat, and the dimensions of the tip 120 may be optimized for different ages of patients or a healthcare practitioner's preference. The handpiece includes a tip coupler component 118 that attaches the tip 120 to the handpiece housing 116. The handpiece further includes a cable coupler 114 configured to couple the handpiece housing 116 to the cable 112 such that the handpiece housing 116 may be removably coupled to the cable 112.

The system 100 includes one or more of imaging components, computing components, illumination components, and communication components installed in or on the housing 102. The system 100 includes a computer disposed within the housing 102, which may specifically include one or more single-board computer (SBC) such as a Raspberry Pi® (Raspberry Pi® is a trademark of Raspberry Pi Ltd).

The cable 112 includes wiring for enabling electrical communication between a computer disposed within the housing 102 and an image sensor disposed within the handpiece unit. The cable 112 may additionally include a fiber optic cable for communicating electromagnetic radiation (EMR) from a light source disposed within the housing 102 to a distal end of the handpiece unit. The cable 112 may additionally include tubing configured to receive a fluid. In some implementations, air is pushed through the tubing and out through the tip 120. If an examiner is attempting to inspect a patient's internal ear components, then this puff of air enables the examiner to test mobility of the patient's tympanic membrane.

The tip 120 is easily removable and may be exchanged for a tip 120 with different dimensions, magnification power, or configurations for different visualization implementations. The tip 120 may include a disposable tip that is removed and exchanged for each visualization session. The tip 120 may be configured to be disposed within and/or surrounded by a disposable protective sleeve that may be used and then discarded after each visualization session.

The tip 120 may additionally include a magnifying lens. In some implementations, the magnifying lens is disposed within the tip coupler component 118. The magnifying lens may specifically have a power of about 8 diopters (3.00× magnification) or more. It should be appreciated that the power of the magnification may be optimized for different imaging techniques, including the ear, nose, and throat imaging techniques described herein. The power of the magnifying lens may be tuned based on standard procedures for visualizing the ear canal, nose, or throat of a patient. The tip 120 may include multiple removable magnifying lenses that may be swapped in and out depending on the visualization needs. The system 100 may additionally provide digital magnification with the image sensor to zoom into certain portions of a scene to view additional details of the patient's ear, nose, or throat regions.

The tip 120 may be configured for visualizing a patient's external acoustic meatus (EAC) or ear canal. In this case, the tip 120 includes an otoscope or auriscope used for looking inside a patient's ears. The tip 120 enables an image sensor to capture images of the ear canal and tympanic membrane or eardrum. Because the eardrum is the border separating the external ear canal from the middle ear, its characteristics can be indicative of various diseases of the middle ear space that may be identifiable with the system 100.

The tip 120 may be configured for visualization of a patient's nasal passageway. In some cases, the tip 120 for nasal visualization includes a narrow and flexible endoscope. The endoscope may be equipped with one or more fiber optic cables for transmitting light from the light source to the interior of the patient's nasal cavity. The endoscope enables an examiner to view the nasal septum and turbinates of the patient, and to examine where the sinuses drain into the nose, the posterior nasal cavity, and the nasopharynx.

The tip 120 may be configured for visualization of a patient's oral cavity. In some cases, the tip 120 for oral cavity visualization includes a narrow and flexible endoscope. A practitioner, assistant, or patient may be instructed to guide the narrow and flexible endoscope throughout the patient's oral cavity and/or into the patient's throat, depending on which components of the patient's oral cavity need to be visualized.

The system 100 includes one or more image sensors. The image sensor may be disposed within a distal end or proximal end of the handpiece housing 116. In specific implementations, the image sensor is disposed within the tip 120 and may specifically be disposed within the tip coupler component 118. The image sensor may include a charge-coupled device (CCD) or an active-pixel sensor (CMOS sensor). The image sensor may include a pixel array having a color filter array that permits red, green, and blue visible light wavelengths to interact with selected pixels of the pixel array. Each individual pixel sensor element may be made sensitive to red, green, or blue wavelengths to return image data for that wavelength of light, and in turn, the image sensor can return a Red-Green-Blue (RGB) color video stream. The image sensor may continually capture image frames to generate a real-time video stream of the ear canal, nasal cavity, and/or oral cavity as needed.

In an implementation, the system 100 includes one or more image sensors disposed within the tip 120 or the tip coupler component 118. The image sensor communicates with a computer disposed within the housing 102 by way of the cable 112. The cable 112 provides a bidirectional electrical communication between the image sensor and the computer disposed within the housing. The computer may be configured to configure and instruct the image sensor to capture a series of images to generate a video stream. The computer may then provide the video stream to a provider over a network connection in real-time or near real-time.

The image sensor may communicate with a controller. The controller communicates with one or more image sensors and receives image data therefrom. The controller may receive raw pixel readout data and generate a color video stream by processing the raw pixel readout data through an image signal processing pipeline. The image sensors may include on-chip processing of image data, and in this case, the controller may receive a processed video stream rather than raw pixel readout data.

The controller may perform image processing on the images output by the image sensor. In some cases, a practitioner may remotely instruct the controller to perform digital zoom operations with an image sensor. In these cases, the controller may enlarge pixel sizes and/or crop the output image to enable the practitioner to see certain components with a larger image. The controller may additionally perform other real-time image adjustments, including white balance, exposure, clarity, contrast, and so forth.

The system 100 includes a light source disposed within the housing 102 and/or the handpiece unit. In some cases, an examiner is seeking to visualize an internal body cavity of the patient, and the internal body cavity may not receive any ambient light. In these cases, the light source may serve as the only source of light within the light-deficient environment of the patient's internal body cavity, such as the ear canal, nasal cavity, or oral cavity. The light source may include white light emitted by an LED or other light source. In an embodiment, the system 100 includes a central light source which may include one or more bulbs. The light source may be powered by a battery disposed within the housing 102 and/or a direct power source funneled through a computer disposed within the housing 102.

In some implementations, the light source is disposed within the housing 102, and light emitted by the light source travels through a fiber optic cable disposed within the cable 112 and is ultimately emitted through the tip 120. In other implementations, the light source is disposed within the handpiece unit itself and may specifically be disposed within the tip 120 or the tip coupler component 118. The light source may automatically turn on and remain on when the system 100 is turned on by way of the power switch 106. In other implementations, the system 100 includes a power switch and controller for turning the light source on and off. In other implementations, the light source may be turned on and off remotely by communicating with a controller disposed within the housing 102 over the Internet or some other communication means.

The controller is in communication with a network. The controller may communicate with a Wide Area Network (WAN) such as the Internet by way of WiFi™, Bluetooth®, near-field communications, a direct hardwired connection through an Ethernet® connection (see network port 104), and so forth. The controller provides the processed imaging data (which may include a real-time video stream) to the network such that the processed imaging data can be transmitted to an examiner in near real-time and/or stored on remote storage resources. In an example implementation, a patient or assistant will use the system 100 to visualize certain portions of the patient's body, such as the ear canal, the nasal cavity, and/or the oral cavity. The controller causes this data to be transmitted to an examiner (such as an Ear Nose and Throat physician or other healthcare professional) that is located remotely from the patient. The imaging data may be provided to the examiner in near real-time and the examiner may communicate with the patient and/or assistant while the visualization procedure is taking place.

Figure 2A:
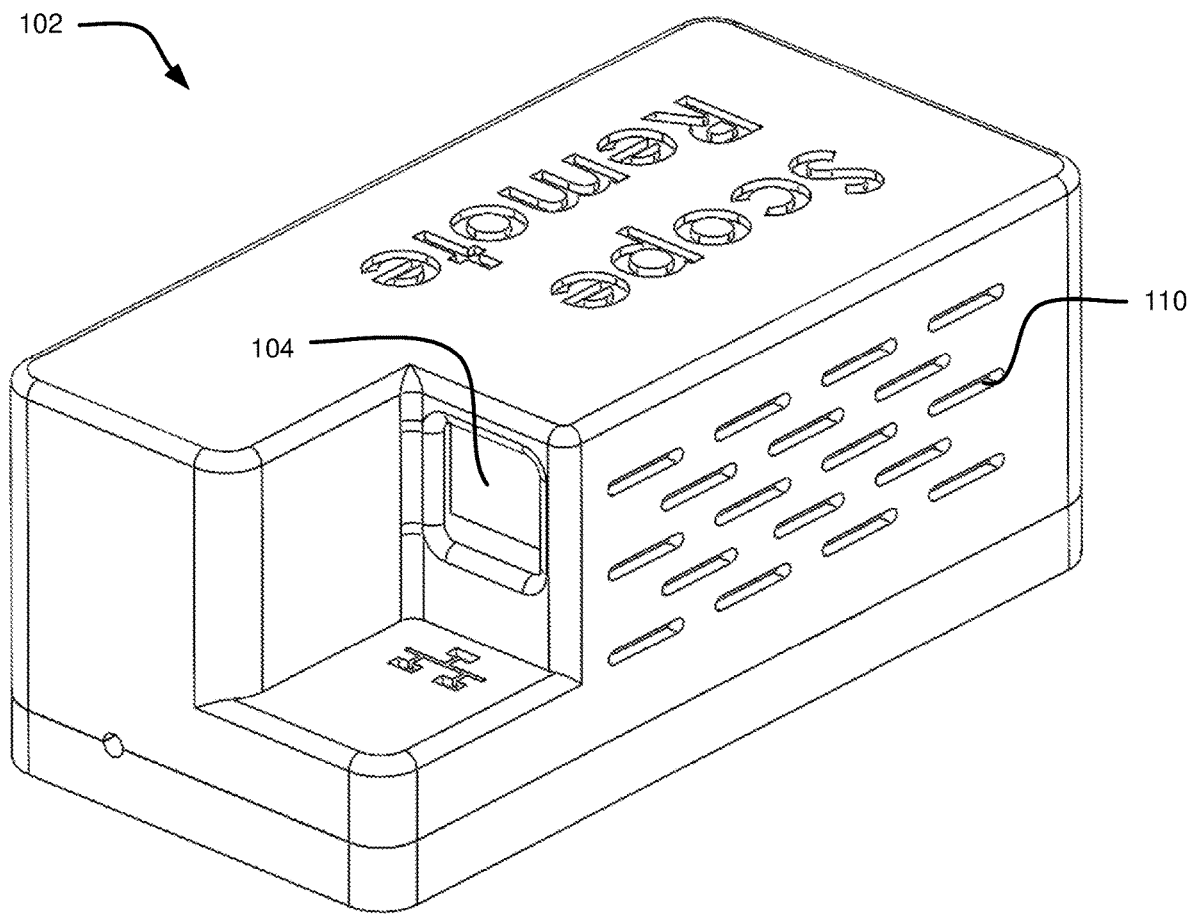
FIGS. 2A-2C are perspective view of a housing configured to protect electrical components of a system for remote visualization of a patient's ear, nose, or throat regions.
Figure 2B:
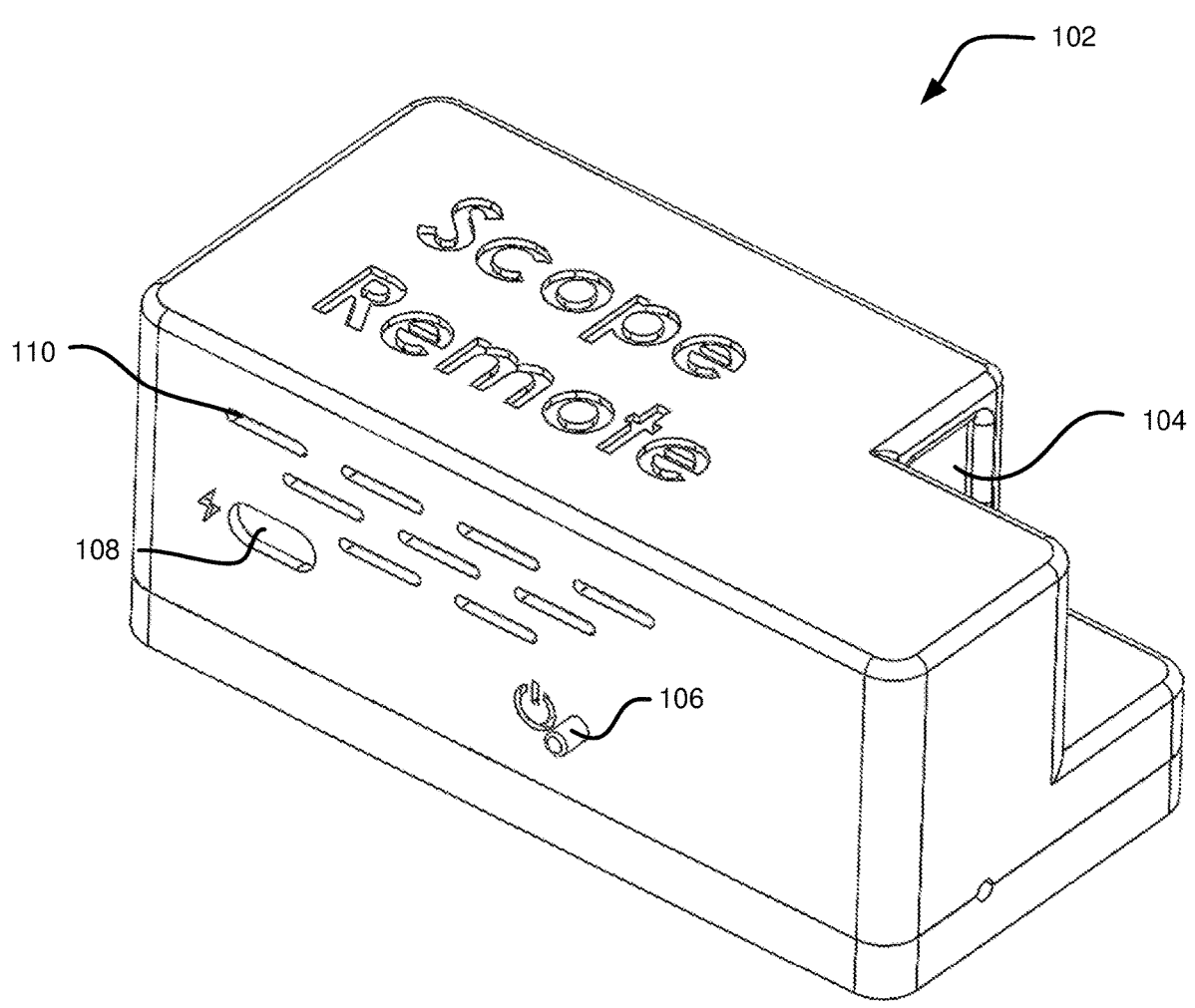
Figure 2C:
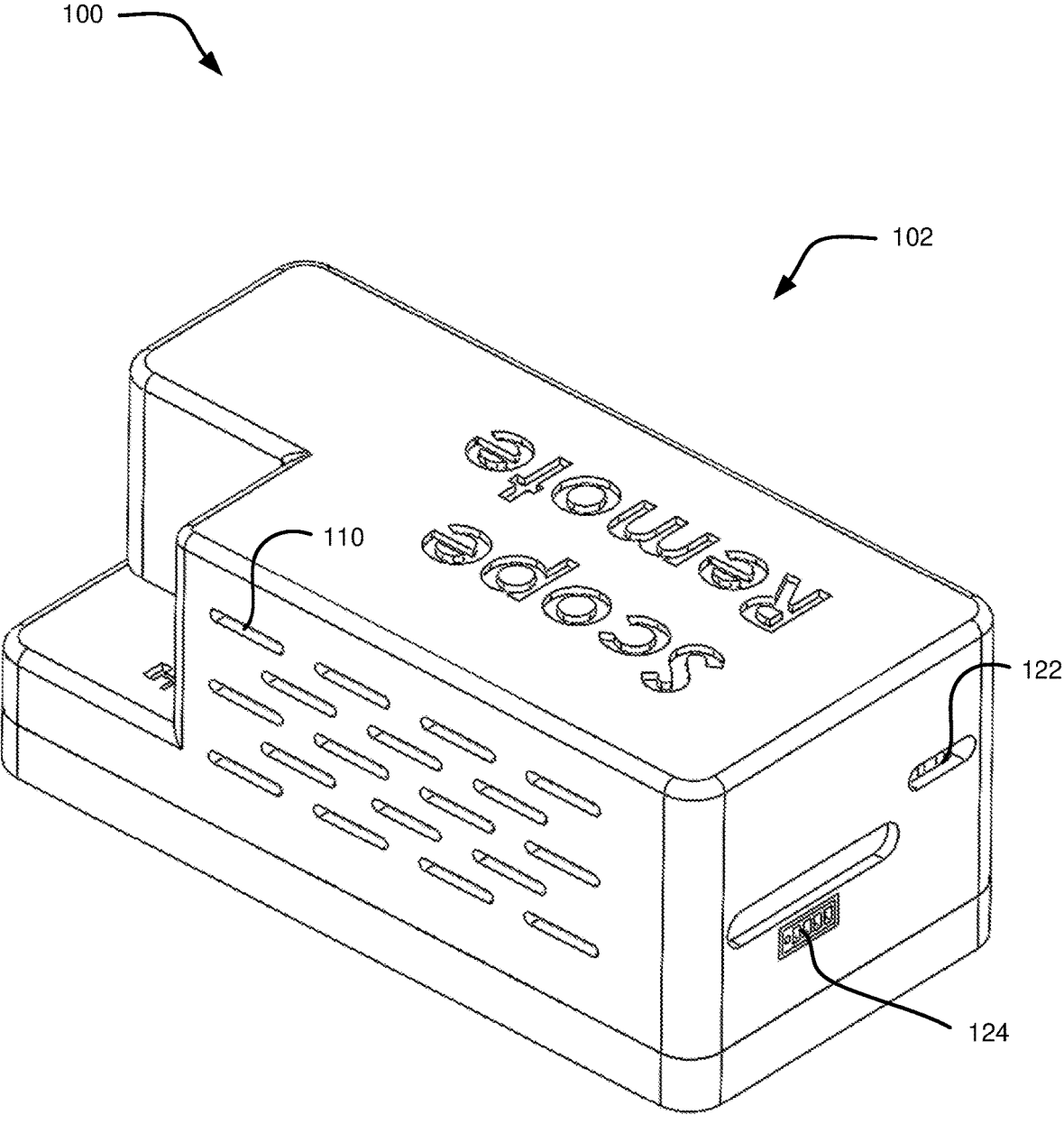

FIGS. 2A-2C are perspective views of the housing 102 portion of the system 100 illustrated in FIG. 1. FIG. 2A is a perspective view showing the vents 110 and network port 104. FIG. 2B is a perspective view showing the same elements pictured in FIG. 1, including the power switch 106, vents 110, and the data port opening 108. FIG. 2C is a perspective view of the housing 102 showing a battery life viewer 124 and another data port opening 122. The battery life viewer 124 enables a viewer to identify the remaining battery life for the system 100 and may specifically include a hole disposed through the housing 102 that enables a user to view the remaining battery life displayed on an electronic component disposed within the housing 102.

Figure 3:
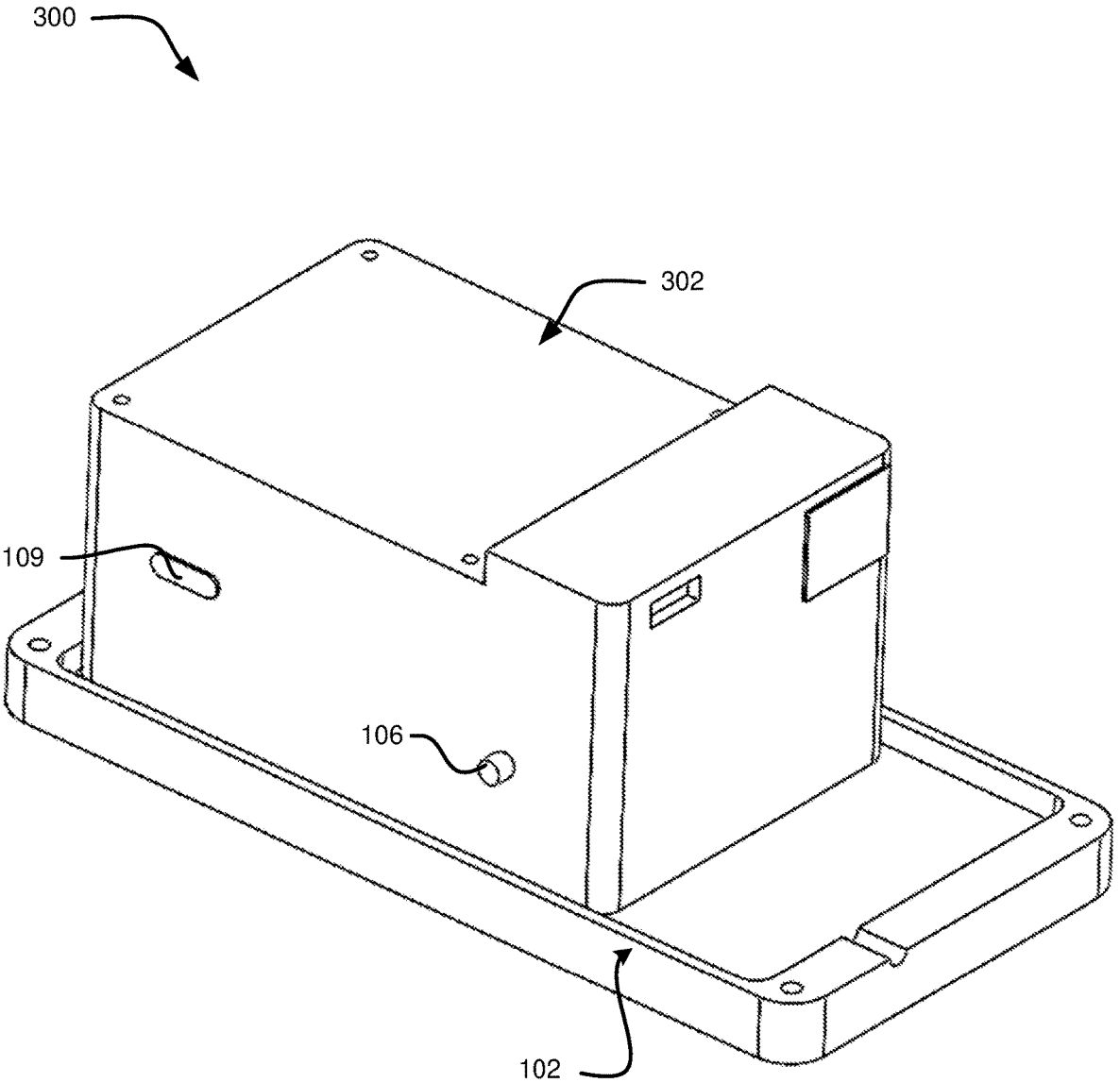
FIG. 3 is a perspective view of internal components and an internal housing for protecting electrical components of a system for remote visualization of a patient's ear, nose, or throat regions.

FIG. 3 is a perspective view of internal components 300 of the system 100. The internal components 300 may be disposed within an internal housing 302 that is attached to a component of the housing 102. The internal housing 302 may consist of an additional piece of plastic or other material to provide protection and support to the electrical components of the system 100.

The internal housing 302 may have a data port opening 109 that corresponds with the data port opening 108 disposed through the housing 102. The electrical components corresponding with the data port openings 108, 109 maybe attached to a wall of the internal housing 302. The data port may include a Universal Serial Bus (USB) type port to enable charging or bidirectional data communication by way of a USB cable connection.

Figure 4:
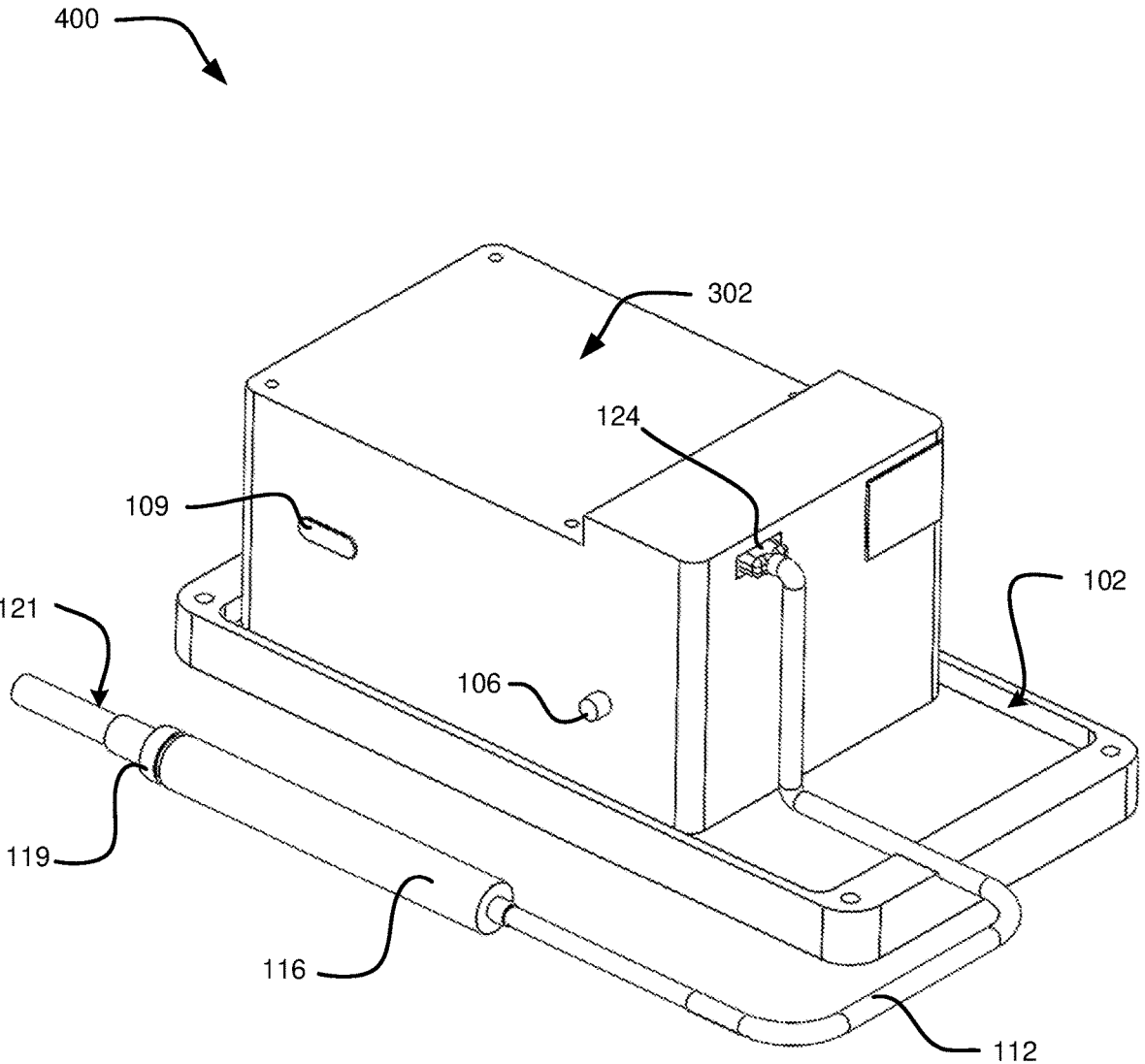
FIG. 4 is a perspective view of internal components and an internal housing for protecting electrical components of a system for remote visualization of a patient's ear, nose, or throat regions.

FIG. 4 is a straight-on view of a side of the housing 102 of the system 100. The housing 102 includes a charge viewer 118 to enable a user to determine the current charge level for the system's 100 battery stores. In the implementation illustrated in FIG. 4, the charge viewer 118 includes a window disposed through a wall of the housing 102 enabling a user to view through the window and see the charge status of a battery pack disposed within the housing 102. The charge viewer 118 may include any digital representation of the charge status of the system's 100 battery.

FIG. 4 is a perspective view of internal components of a system 400 for remote visualization of a patient's ear, nose, or throat regions. The system 400 is like the system 100 illustrated in FIG. 1 but equipped with different components on the handpiece portion. The tip 121 and tip coupler component 119 illustrated in FIG. 4 may include different geometries optimized for visualizing a different anatomical part of a patient. Additionally, the handpiece housing 117 may be optimized with a slightly smaller geometry to that may improve ergonomics or accessibility for certain types of visualization.

The system 400 includes a data connection port 124 enabling electrical communications between a computer disposed within the internal housing and an image sensor disposed within the handpiece unit. The computer may provide instructions to the image sensor to capture images making up a real-time video stream of the patient's anatomy. The image sensor may then provide those images back to the computer by way of the cable 112 and the data connection port 124.

Figure 5:
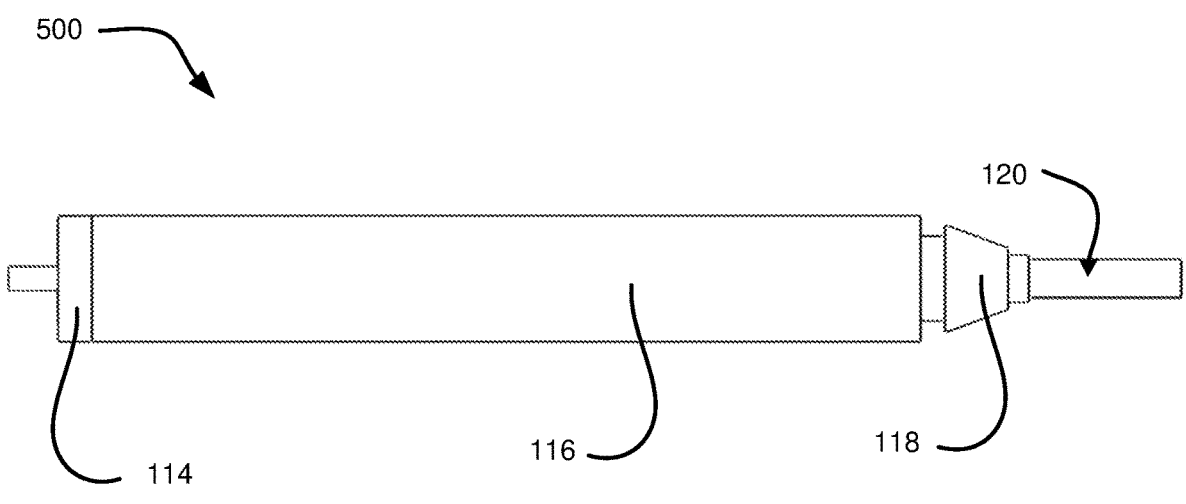
FIG. 5 is a side view of an example handpiece unit of a system for remote visualization of a patient's ear, nose, or throat regions.
Figure 6:
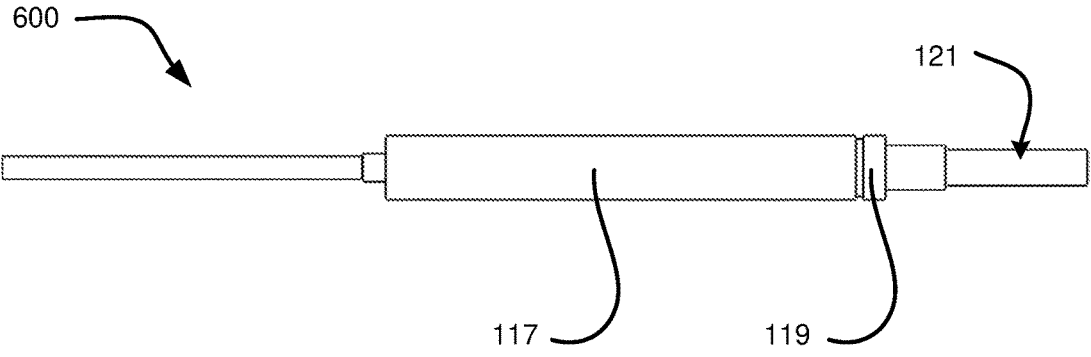
FIG. 6 is a side view of an example handpiece unit of a system for remote visualization of a patient's ear, nose, or throat regions.

FIGS. 5 and 6 are side views of example handpiece units 500, 600 associated with systems 100, 400 for remote visualization of a patient's ear, nose, or throat regions. Each of the handpiece units 500, 600 includes a handpiece housing 116, 117 and a tip 120, 121, whereby the tip 120, 121 may be removably attached to the handpiece housing 116, 117 by way of a tip coupler component 118, 119. The tip 120, 121 may twist on to the tip coupler component 118, 119 and then "click" and engage with the tip coupler component 118, 119. Similarly, the tip coupler component 118, 119 may twist on and then engage with the handpiece housing 116, 117.

The tip 120, 121 may be disposable and/or may with a disposable plastic piece. If the tip 120, 121 is disposable, then the image sensor and light source may be disposed within the handpiece housing 116, 117 or the tip coupler component 118, 119 to ensure the image sensor and light source are not thrown away along with the tip 120, 121.

In some implementations, all system components are disposed within a pen-like structure, such as those illustrated in FIGS. 5 and 6. In these implementations, the controller processing components, network antennas, batteries, and other components will also be disposed within the handpiece housing 116, 117. Thus, the system would not include separate housing structures (see 102, 302) for protecting components separate from the handpiece unit.

The systems described herein are operated with a computer disposed within a housing 102. The housing 102 may be manufactured as two or more separate components that are later combined and releasably connected to one another. The systems 100, 400 includes a processor, which may include one or more of a microcontroller, microprocessor, digital signal processor (DSA), or media processor. The processor may specifically include a single-board computer (SBC).

The systems described herein may be powered with rechargeable batteries that may be disposed within a battery casing. The battery casing may be coupled to other electronic components within the system to provide battery power from the batteries to the processor 120 and other components. The rechargeable batteries may be recharged in a recharging system comprising a charge indicator. In other implementations, the system may be powered with direct (non-battery) power or with non-rechargeable batteries. The system may be powered with any suitable power source known in the art.

Figure 7:
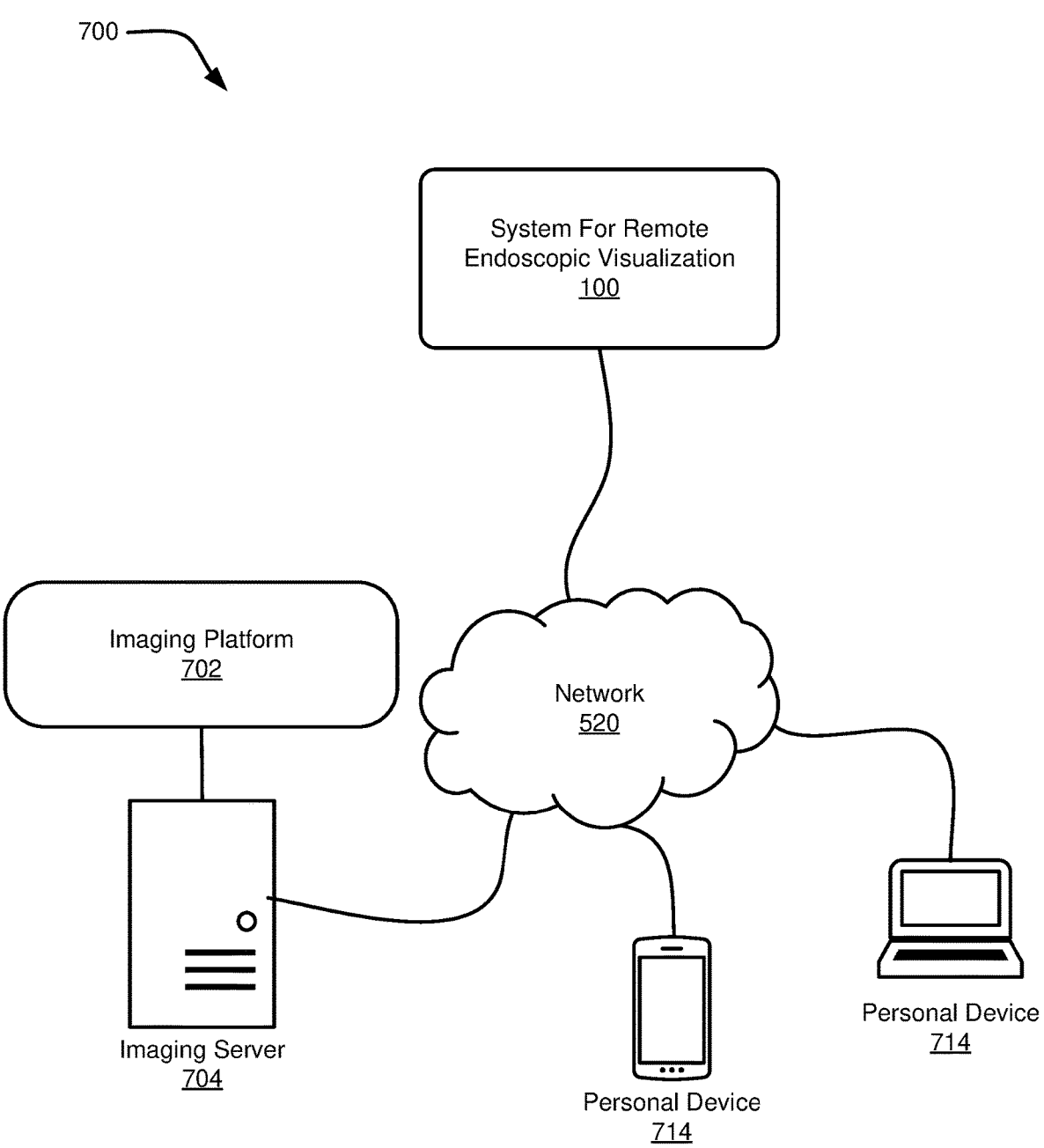
FIG. 7 is a schematic diagram of a system for remote visualization and image processing.

FIG. 7 is a schematic diagram of a system 700 for remote imaging and image analysis. The system 700 includes an imaging server 704 that supports an imaging platform 702. The imaging platform 702 may be accessed by a user interface displayed on a personal device 714. The imaging server 704 is in communication with the system 100 by way of a network 720.

The imaging server 704 provides storage and processing resources to support the imaging platform 702. The imaging platform 702 is a system for viewing, storing, and manipulating imaging data, including image frames and video streams captured by the system 100. The imaging platform 702 includes a user interface that is accessible by way of a website or application by a personal device 714. The imaging server 704 ensures that images captured by the system

100 are stored on a HIPPA (Health Insurance Portability and Accountability Act) client server to ensure that patient data and images are secure.

The imaging server 704 receives input by way of personal devices 714 in communication with the network 720. The imaging server 704 communicates with one or more individual users (e.g., patients, assistants, medical personnel, physicians, hospital administrators, and so forth), and administrators by way of the network 720 connection. The imaging server 704 generates independent accounts on the imaging platform 702. Each of the independent accounts is assigned to a certain user or entity and includes login information for securely accessing the imaging platform 702. In some implementations, one group (e.g., a health system, hospital, group of physicians, and so forth) might have a global account on the imaging platform 702 that may be accessed by certain individuals, and the group may further have individual accounts that are assigned to certain users, e.g., physicians, imaging technicians, surgeons, healthcare personnel, administrators, surgical directors, support staff, and so forth. The imaging platform 702 can assign permissions for certain accounts to have read and/or write access to certain data. The imaging platform 702 also provides accounts to users that are not associated with a group or other entity, and these accounts may be linked to or synced with other entities.

The imaging server 704 may include a neural network and algorithmic instructions for image analysis and predictive modeling. The neural network of the imaging server 704 may be trained on a dataset comprising images and video streams of various nasal cavities, oral cavities, ear canals, and so forth, and may specifically be trained on images and video streams that might be captured by the system 100 as described herein. The neural network may be trained to analyze image data to identify certain tissues, organ structures, abnormalities, and so forth.

The personal device 714 includes any suitable means for accessing the imaging platform 702 over the network. The personal device 714 includes, for example, mobile phones, laptops, personal computers, tablets, applications, and so forth.

The network 720 includes a computing network that enables the transfer of data between independent processor instances. The network 720 may include a cloud computing network accessible over a wide area network or the Internet. The network 720 may include a local area network.

The imaging platform 702 serves as a peer-to-peer video conferencing platform. The system 700 provides real-time communication between two or more personal devices 714, including a personal device 714 associated with a practitioner (such as an ENT physician or other healthcare professional), and another personal device 714 associated with a patient. Any number of personal devices 714 and/or accounts may communicate with the imaging server 704 to view an output video stream in real-time, communicate with other users, and receive instructions from the practitioner.

In some implementations, the practitioner may use two or more personal devices 714 at one time when communicating with a patient over the imaging platform 702. In an alternative implementation, the practitioner uses a single personal device 714, and the user interface on this one personal device 714 presents two "screens" or views. One screen enables the practitioner to view the patient and speak with the patient, while the other screen enables the practitioner to view the images output by the camera of the system 100. The practitioner may then provide real-time instructions to the image sensor and/or the system 100 by way of the network 520 connection.

Figure 8:
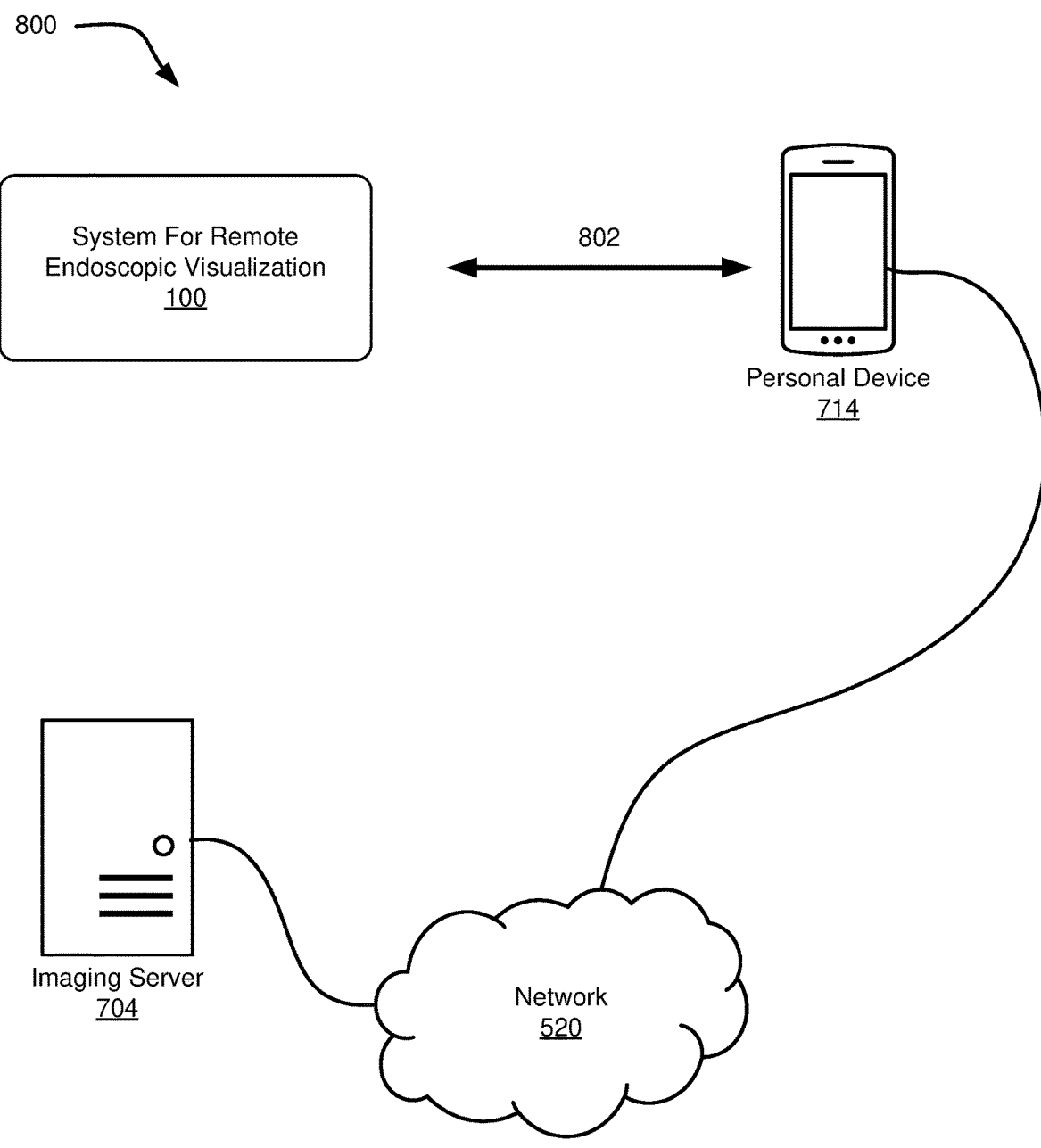
FIG. 8 is a schematic diagram of a system for remote visualization and imaging processing.

FIG. 8 is a schematic diagram of a system 800 for facilitating communications 802 between the system 100 and a personal device 714, and further facilitating communications to the imaging server 704 by way of the network 720. In an embodiment, a user may install an imaging application on a personal device 714 such as a mobile phone or personal computer, and the imaging application may communicate 802 directly with the system 100. The communication 802 channel may include WiFi®, Bluetooth®, near field communication, or some other suitable means of data transfer. The personal device 714 may be connected to the network 720 (such as the Internet) by way of WiFi®, Long-Term Evolution (LTE) telecommunication, or some other suitable means of data transfer to the network 720. The data captured by the system 100 can thereby be transferred to the personal device 714, and to the network 720, and to the imaging server 704. The data may then be accessed remotely from the imaging server 704.

In an example implementation, a patient or assistant uses the system 100 to capture images of the patient's nasal cavity, ear canal, oral cavity, or other region. This data is uploaded to the imaging server 704 and may then be viewed by a physician or imaging technician that is located remotely to the patient. The imaging data can be provided from the system 100 to the remotely located examiner (i.e., the physician, imaging technician, and so forth) in real-time while the system 100 is used to capture images of the patient.

The imaging server 704 may further facilitate communications between the patient/assistant by way of the application installed on the personal device 714. In an example implementation, the application enables real-time communications between the examiner and the patient by way of voice, text, and/or video messaging. The examiner (e.g., the physician, imaging technician, and so forth) may speak to the patient in real-time and assist the patient or assistant in using the system 100 to capture images of the patient's body while the examiner receives images captured by the system 100 in real-time.

Figure 9:
FIG. 9 is a schematic diagram of a system and process flow for remote visualization and imaging processing.

FIG. 9 is a schematic diagram of a process flow 900 for imaging processing and enabling remote visualization of a patient. The process flow 900 includes performing imaging processing 908 on or more of nasal cavity camera 902 data, external auditory canal camera 904 data, and oral cavity camera 906 data. After the images are process 908, the data is communicated from the system 100 to the patient's phone at 910. This data may be communicated by way of WiFi®, Bluetooth®, near field communication, or some other means of communication. The data is received by the remote imaging application 912 installed on the patient's phone. The remote imaging application 912 may cause the data to be transmitted to the imaging server 904.

Figure 10:
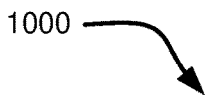
FIG. 10 is a schematic flow chart diagram of a method for audiovisual teleconferencing with image data captured by a medical scope.
Figure 10:
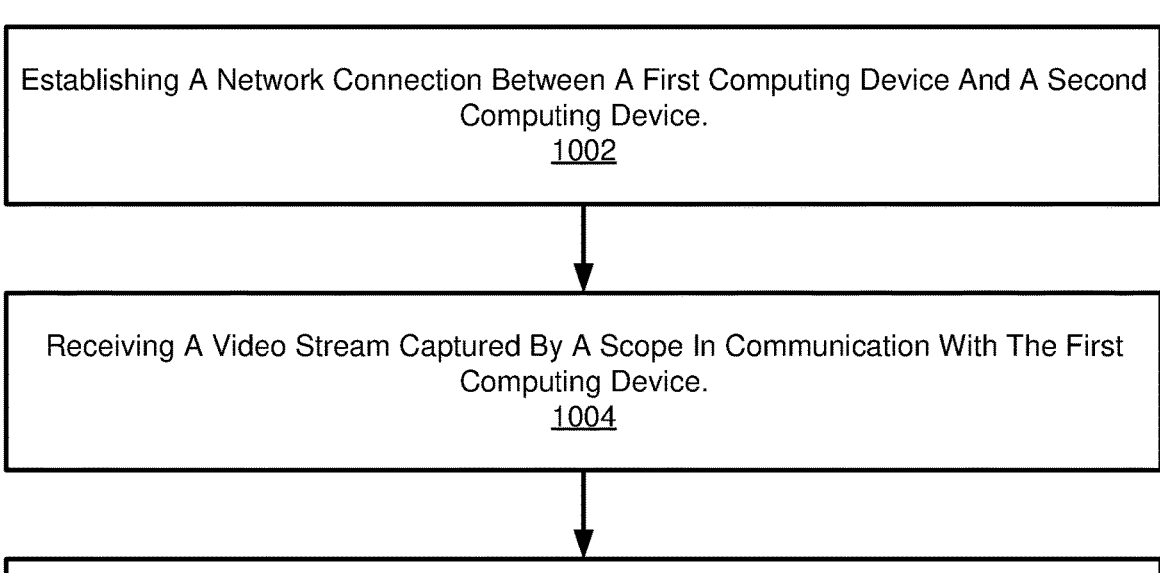

FIG. 10 is a schematic flow chart diagram of a method 1000 for remote visualization and assessment of images captured by a medical scope. The method 1000 includes establishing at 1002 a network connection between a first computing device and a second computing device. The first computing device and the second computing device may include, for example, a mobile phone, personal computer, tablet computer, and so forth. Each of the first computing device and the second computing device may include one or more of a speaker, display, microphone, and camera, and may further include means to transmit and receive a text-based message. Each of the first computing device and the second computing may include a network interface that enables the computing device to connect to a wide area network (WAN) such as the Internet. The network connection between the first computing device and the second computing device may include one or more cloud-based servers communicating with the first computing device and the second computing device by way of the Internet.

The method 1000 continues with receiving at 1004 a video stream captured by a scope in communication with the first computing device. The scope may include the system 100 described herein. The scope may include a medical scope such as an otoscope or a rhino laryngoscope. The medical scope may include an image sensor, light source, network interface, and processor configured to receive images captured by the image sensor and provide those images to a cloud-based server.

The method 1000 continues with providing at 1006 the video stream to each of the first computing device and the second computing device in near real-time. The video stream may be provided to each of the first computing device and the second computing device through an audiovisual teleconference serviced by a remote server. In this case, a user associated with each of the first computing device and the second computing device may view the video stream in near real-time while the video stream is being captured with the scope. At least one of the first computing device or the second computing device is located remote with respect to the scope.

Figure 11:
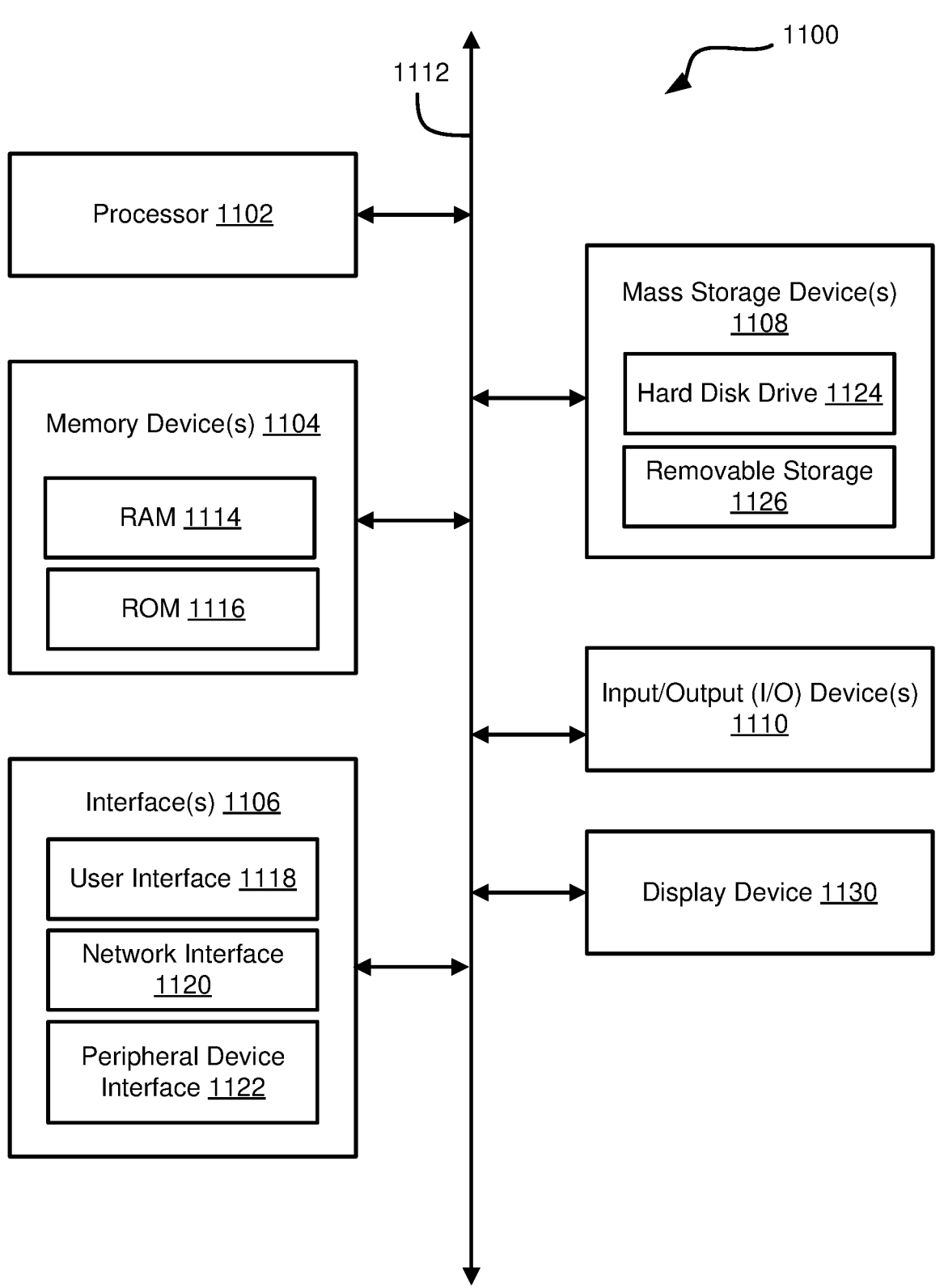
FIG. 11 is a schematic diagram illustrating components of an example computing device.

Referring now to FIG. 11, a block diagram of an example computing device 1100 is illustrated. Computing device 1100 may be used to perform various procedures, such as those discussed herein. Computing device 1100 can perform various monitoring functions as discussed herein, and can execute one or more application programs, such as the application programs or functionality described herein. Computing device 1100 can be any of a wide variety of computing devices, such as a desktop computer, in-dash computer, vehicle control system, a notebook computer, a server computer, a handheld computer, tablet computer and the like.

Computing device 1100 includes one or more processor(s) 1112, one or more memory device(s) 1112, one or more interface(s) 1116, one or more mass storage device(s) 1120, one or more Input/output (I/O) device(s) 1110, and a display device 1130 all of which are coupled to a bus 1112. Processor(s) 1112 include one or more processors or controllers that execute instructions stored in memory device(s) 1112 and/or mass storage device(s) 1120. Processor(s) 1112 may also include various types of computer-readable media, such as cache memory.

Memory device(s) 1112 include various computer-readable media, such as volatile memory (e.g., random access memory (RAM) 1114) and/or nonvolatile memory (e.g., read-only memory (ROM) 1116). Memory device(s) 1112 may also include rewritable ROM, such as Flash memory.

Mass storage device(s) 1120 include various computer readable media, such as magnetic tapes, magnetic disks, optical disks, solid-state memory (e.g., Flash memory), and so forth. As shown in FIG. 11, a particular mass storage device 1120 is a hard disk drive 1124. Various drives may also be included in mass storage device(s) 1120 to enable reading from and/or writing to the various computer readable media. Mass storage device(s) 1120 include removable media 1126 and/or non-removable media.

I/O device(s) 1110 include various devices that allow data and/or other information to be input to or retrieved from computing device 1100. Example I/O device(s) 1110 include cursor control devices, keyboards, keypads, microphones, monitors or other display devices, speakers, printers, network interface cards, modems, and the like.

Display device 1130 includes any type of device capable of displaying information to one or more users of computing device 1100. Examples of display device 1130 include a monitor, display terminal, video projection device, and the like.

Interface(s) 1116 include various interfaces that allow computing device 1100 to interact with other systems, devices, or computing environments. Example interface(s) 1116 may include any number of different network interfaces 1120, such as interfaces to local area networks (LANs), wide area networks (WANs), wireless networks, and the Internet. Other interface(s) include user interface 1118 and peripheral device interface 1122. The interface(s) 1116 may also include one or more user interface elements 1118. The interface(s) 1116 may also include one or more peripheral interfaces such as interfaces for printers, pointing devices (mice, track pad, or any suitable user interface now known to those of ordinary skill in the field, or later discovered), keyboards, and the like.

Bus 1112 allows processor(s) 1112, memory device(s) 1112, interface(s) 1116, mass storage device(s) 1120, and I/O device(s) 1110 to communicate with one another, as well as other devices or components coupled to bus 1112. Bus 1112 represents one or more of several types of bus structures, such as a system bus, PCI bus, IEEE bus, USB bus, and so forth.

For purposes of illustration, programs and other executable program components are shown herein as discrete blocks, such as block 302 for example, although it is understood that such programs and components may reside at various times in different storage components of computing device 1100 and are executed by processor(s) 1102. Alternatively, the systems and procedures described herein, including programs or other executable program components, can be implemented in hardware, or a combination of hardware, software, and/or firmware. For example, one or more application specific integrated circuits (ASICs) can be programmed to carry out one or more of the systems and procedures described herein.

EXAMPLES

Example 1 is a system. The system includes a scope comprising an image sensor and a processor in electronic communication with the image sensor. The processor is configured to execute instructions comprising receiving an image output by the image sensor and providing the image to a remote server by way of a network connection. The remote server communicates the image to each of a first computing device and a second computing device in near real-time.

Example 2 is a system as in Example 1, wherein the first computing device is associated with a first user that captures the image with the scope, and wherein the processor provides the image to the remote server in near real-time after the image is captured by the first user.

Example 3 is a system as in any of Examples 1-2, wherein the second computing device is associated with a second user that views the image captured with the scope, and wherein the remote server communicates the image to each of the first computing device and the second computing device in near real-time after the image is captured by the first user.

Example 4 is a system as in any of Examples 1-3, further comprising an otoscope tip configured to enable visualization of an external auditory canal of a user.

Example 5 is a system as in any of Examples 1-4, further comprising a rhino laryngoscope tip configured to enable visualization of an interior of one or more of a nasal passageway or a throat of a user.

Example 6 is a system as in any of Examples 1-5, further comprising a scope tip, wherein the scope tip is optimized for visualization of one or more of an external auditory canal, a nasal passageway, or a throat of a user.

Example 7 is a system as in any of Examples 1-6, further comprising a light source and a fiber optic cable, wherein the fiber optic cable carries electromagnetic radiation from the light source to a distal end of the scope tip.

Example 8 is a system as in any of Examples 1-7, further comprising a light source disposed within the scope tip.

Example 9 is a system as in any of Examples 1-8, wherein the image sensor is disposed within the scope tip.

Example 10 is a system as in any of Examples 1-9, further comprising a handpiece housing and a scope tip removably attached to the handpiece housing.

Example 11 is a system as in any of Examples 1-10, wherein the image sensor is disposed within the handpiece housing.

Example 12 is a system as in any of Examples 1-11, wherein the processor comprises one or more single-board computers.

Example 13 is a system as in any of Examples 1-12, wherein the instructions further comprise compressing the image and packaging the image within a data packet to be transmitted over the Internet to the remote server.

Example 14 is a system as in any of Examples 1-13, wherein the instructions further comprise adjusting one or more of white balance, exposure, or gain on the image prior to providing the image to the remote server by way of the network connection.

Example 15 is a system as in any of Examples 1-14, further comprising a housing, wherein the processor is disposed within an interior space of the housing.

Example 16 is a system as in any of Examples 1-15, further comprising: a handpiece housing configured to be held by a user; and a scope tip removably attached to the handpiece housing; wherein the handpiece housing and the scope tip are external to the housing comprising the processor.

Example 17 is a system as in any of Examples 1-16, further comprising a cable that provides electronic communication between the image sensor and the processor.

Example 18 is a system as in any of Examples 1-17, further comprising a rechargeable battery.

Example 19 is a system as in any of Examples 1-18, further comprising a flexible tube configured to be inserted into one or more of a nasal passageway or a throat of a user, and wherein the image sensor is disposed at a distal end or a proximal end of the flexible tube.

Example 20 is a system as in any of Examples 1-19, further comprising a fiber optic cable disposed within the flexible tube configured to carry electromagnetic radiation from a light source to the distal end of the flexible tube.

Example 21 is a method. The method includes establishing a network connection between a first computing device and a second computing device. The method includes receiving a video stream captured by a scope in communication with at least one of the first computing device. The method includes providing the video stream to each of the first computing device and the second computing device in real-time.

Example 22 is a method as in Example 21, wherein the first computing device is associated with a first user capturing the video stream with the scope, and wherein the second computing device is associated with a second user that remotely views the video stream captured with the scope.

Example 23 is a method as in any of Examples 21-22, wherein the scope is an otoscope.

Example 24 is a method as in any of Examples 21-23, wherein the scope is a rhino laryngoscope.

Example 25 is a method as in any of Examples 21-24, wherein establishing the network connection between the first computing device and the second computing device comprises establishing a cloud-based conference between the first computing device and the second computing device.

Example 26 is a method as in any of Examples 21-25, wherein the cloud-based conference comprises one or more of a video conference or an audio conference.

Example 27 is a method as in any of Examples 21-26, wherein the cloud-based conference is processed by a server in communication with the Internet, and wherein each of the first computing device and the second computing device communicate with the server by way of the Internet.

Example 28 is a method as in any of Examples 21-27, further comprising compressing the video stream captured by the scope.

Example 29 is a method as in any of Examples 21-28, further comprising packaging the compressed video stream into a data packet to be transmitted over the network connection.

Example 30 is a method as in any of Examples 21-29, further comprising rendering a user interface for a medical teleconferencing platform, wherein the medical teleconferencing platform enables a first user associated with the first computing device to join an audiovisual conference with a second user associated with the second computing device.

Example 31 is a method as in any of Examples 21-30, wherein the first user captures the video stream with the scope, and wherein the method comprises: receiving a message comprising one or more of an audio message, a text message, or an audiovisual message from the second computing device to be provided to the first computing device in real-time; providing the message to the first computing device in real-time while continuing to provide the video stream to each of the first computing device and the second computing device in real-time.

Example 32 is a method as in any of Examples 21-31, wherein the scope is an otoscope, and wherein the video stream comprises a plurality of images of a first user's external auditory canal captured with the scope and provided to each of the first computing device and the second computing device in real-time.

Example 33 is a method as in any of Examples 21-32, wherein the scope is a rhino laryngoscope, and wherein the video stream comprises a plurality of images of one or more of a first user's nasal passageway or throat captured with the scope and provided to each of the first computing device and the second computing device in real-time.

Example 34 is a method as in any of Examples 21-33, further comprising encrypting the video stream.

Example 35 is a method as in any of Examples 21-34, further comprising storing the video stream on a cloud-based storage resource.

Example 36 is a method as in any of Examples 21-35, further comprising applying permissions to the video stream stored on the cloud-based storage resource such that only authorized persons may read or write to the video stream.

Example 37 is a method as in any of Examples 21-36, further comprising processing the video stream to adjust one or more of exposure, white balance, or gain in real-time prior to providing the video stream to each of the first computing device and the second computing device.

Example 38 is a method as in any of Examples 21-37, further comprising establishing a network connection between the scope and the first computing device.

Example 39 is a method as in any of Examples 21-38, wherein the network connection between the scope and the first computing device comprises one or more of a Bluetooth® connection, an Internet connection enabled by a WiFi® connection, or a hardwired connection.

Example 40 is a method as in any of Examples 21-39, wherein establishing the network connection between the first computing device and the second computing device comprises: connecting the first computing device to a remote server by way of the Internet; and connecting the second computing device to the remote server by way of the Internet; wherein the first computing device and the second computing device receive the video stream in real-time by way of a medical teleconferencing application executed by the remote server.

Example 41 is a system. The system includes a scope comprising an image sensor and a processor in electronic communication with the image sensor. The processor is configured to execute instructions comprising receiving an image output by the image sensor; and providing the image to a remote server by way of a network connection. The remote server communicates the image to each of a first computing device and a second computing device in near real-time.

Example 42 is a system as in Example 41, wherein the first computing device is associated with a first user that captures the image with the scope, and wherein the processor provides the image to the remote server in near real-time after the image is captured by the first user.

Example 43 is a system as in any of Examples 41-42, wherein the second computing device is associated with a second user that views the image captured with the scope, and wherein the remote server communicates the image to each of the first computing device and the second computing device in near real-time after the image is captured by the first user.

Example 44 is a system as in any of Examples 41-43, wherein the scope comprises: a handpiece housing; a removable scope tip releasably attached to a distal end of the handpiece housing; wherein the removable scope tip is configured to enable visualization of one or more of an external auditory canal of a user, a nasal passageway of the user, or a throat of the user.

Example 45 is a system as in any of Examples 41-44, wherein the removable scope tip comprises one or more of an otoscope tip, a rhino laryngoscope tip, or a flexible endoscope.

Example 46 is a system as in any of Examples 41-45, wherein the processor is disposed within a housing remote from the handpiece housing; wherein the image sensor is disposed within the handpiece housing; and wherein the system further comprises a cable providing the electronic communication between the image sensor and the processor.

Example 47 is a system as in any of Examples 41-46, further comprising a light source disposed within the handpiece housing.

Example 48 is a system as in any of Examples 41-47, further comprising a light source and a fiber optic cable, wherein the fiber optic cable carries electromagnetic radiation from the light source to a distal end of the scope tip.

Example 49 is a system as in any of Examples 41-48, wherein the processor comprises one or more single-board computers.

Example 50 is a system as in any of Examples 41-49, wherein the instructions further comprise compressing the image and packaging the image within a data packet to be transmitted over the Internet to the remote server.

Example 51 is a system as in any of Examples 41-50, wherein the instructions further comprise adjusting one or more of white balance, exposure, or gain on the image prior to providing the image to the remote server by way of the network connection.

Example 52 is a system as in any of Examples 41-50, further comprising: a housing, wherein the processor is disposed within an interior space defined by the housing; a handpiece housing configured to be held by a user; and a scope tip removably attached to the handpiece housing; wherein the handpiece housing and the scope tip are external to the housing comprising the processor.

Example 53 is a system as in any of Examples 41-52, further comprising a flexible tube configured to be inserted into one or more of a nasal passageway or a throat of a user, and wherein the image sensor is disposed at a distal end or a proximal end of the flexible tube.

Example 54 is a system as in any of Examples 41-53, further comprising a fiber optic cable disposed within the flexible tube configured to carry electromagnetic radiation from a light source to the distal end of the flexible tube.

Example 55 is a system as in any of Examples 41-54, further comprising: a handpiece housing configured to be held by a user; a removable scope tip attached to the handpiece housing, wherein the removable scope tip is configured to enable visualization of one or more of an external auditory canal of a user, a nasal passageway of the user, or a throat of the user; the image sensor disposed within the handpiece housing; and the processor disposed within the handpiece housing.

Example 56 is a system as in any of Examples 41-55, further comprising the remote server in communication with the first computing device and the second computing device, wherein the remote server is configured to execute instructions stored in non-transitory computer readable storage medium, the instructions comprising: establishing a network connection between the first computing device and the second computing device; receiving a video stream captured by the image sensor of the scope; providing the video stream to each of the first computing device and the second computing device in real-time.

Example 57 is a system as in any of Examples 41-56, wherein the instructions are such that establishing the network connection between the first computing device and the second computing device comprises establishing one or more of a video conference or an audio conference via a cloud-based conferencing system.

Example 58 is a system as in any of Examples 41-57, wherein the instructions further comprise: rendering a user interface for a medical teleconferencing platform, wherein the medical teleconferencing platform enables a first user associated with the first computing device to join an audiovisual conference with a second user associated with the second computing device; wherein the first user captures the video stream with the image sensor of the scope in real-time while communicating with the second user of the medical teleconferencing platform.

Example 59 is a system as in any of Examples 41-58, wherein the instructions further comprise: encrypting a recording of the video stream; storing the recording of the video stream on a cloud-based storage resource; and applying permissions to the cloud-based storage resource such that only authorized persons may read or write to the recording of the video stream.

Example 60 is a system as in any of Examples 41-59, further comprising one or more network antennas, wherein the one or more network antennas enable: the processor to communicate with the remote server by way of a wireless or wired Internet connection; and the processor to communicate with a mobile device by way of a Bluetooth® connection.

In the above disclosure, reference has been made to the accompanying drawings, which form a part hereof, and in which is shown by way of illustration specific implementations in which the disclosure may be practiced. It is understood that other implementations may be utilized, and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Implementations of the systems, devices, and methods disclosed herein may comprise or utilize a special purpose or general-purpose computer including computer hardware, such as, for example, one or more processors and system memory, as discussed herein. Implementations within the scope of the present disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium, which can be used to store desired program code means in the form of computer-executable instructions or data structures and which can be accessed by a general purpose or special purpose computer.

An implementation of the devices, systems, and methods disclosed herein may communicate over a computer network. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links, which can be used to carry desired program code means in the form of computer-executable instructions or data structures and which can be accessed by a general purpose or special purpose computer. Combinations of the above should also be included within the scope of computer-readable media.

Computer-executable instructions comprise, for example, instructions and data which, when executed at a processor, cause a general-purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, an in-dash vehicle computer, personal computers, desktop computers, laptop computers, message processors, handheld devices, multi-processor systems, microprocessor-based or programmable consumer electronics, network PCs, minicomputers, mainframe computers, mobile telephones, PDAs, tablets, pagers, routers, switches, various storage devices, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the description and claims to refer to particular system components. The terms "modules" and "components" are used in the names of certain components to reflect their implementation independence in software, hardware, circuitry, sensors, or the like. As one skilled in the art will appreciate, components may be referred to by different names. This document does not intend to distinguish between components that differ in name, but not function.

It should be noted that the sensor embodiments discussed above may comprise computer hardware, software, firmware, or any combination thereof to perform at least a portion of their functions. For example, a sensor may include computer code configured to be executed in one or more processors and may include hardware logic/electrical circuitry controlled by the computer code. These example devices are provided herein purposes of illustration and are not intended to be limiting. Embodiments of the present disclosure may be implemented in further types of devices, as would be known to persons skilled in the relevant art(s).

At least some embodiments of the disclosure have been directed to computer program items comprising such logic (e.g., in the form of software) stored on any computer useable medium. Such software, when executed in one or more data processing devices, causes a device to operate as described herein.

While various embodiments of the present disclosure have been described above, it should be understood they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments but should be defined only in accordance with the following claims and their equivalents. The foregoing description has been presented for the purposes of illustration and description. It is not intended to be exhaustive or to limit the disclosure to the precise form disclosed. Many modifications and variations are possible in light of the above teaching. Further, it should be noted that any or all the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A system comprising:
a scope comprising an image sensor, wherein the system is associated with a first user;
a processor in electronic communication with the image sensor;
wherein the processor is configured to execute instructions comprising:
receiving an image output by the image sensor;
providing the image to a remote server by way of a network connection; and
receiving instructions from a second computing device associated with a second user to control the image sensor of the scope in near real-time; and
wherein the remote server communicates the image to each of a first computing device, associated with the first user, and the second computing device in near real-time, and wherein the system, the second computing device, and the remote server, are located physically remote to one another.

2. The system of claim 1, wherein the first computing device is associated with a first user that captures the image with the scope, and wherein the processor provides the image to the remote server in near real-time after the image is captured by the first user.

3. The system of claim 2, wherein the second computing device is associated with a second user that views the image captured with the scope, and wherein the remote server communicates the image to each of the first computing device and the second computing device in near real-time after the image is captured by the first user.

4. The system of claim 1, wherein the scope comprises:
a handpiece housing;
a removable scope tip releasably attached to a distal end of the handpiece housing;
wherein the removable scope tip is configured to be removed and exchanged for a different type of scope tip to enable visualization of one or more of an external auditory canal of a user, a nasal passageway of the user, or a throat of the user.

5. The system of claim 4, wherein the removable scope tip and the different type of scope tip comprises one or more of an otoscope tip, a rhino laryngoscope tip, or a flexible endoscope.

6. The system of claim 4, wherein the processor is disposed within a housing remote from the handpiece housing;
wherein the image sensor is disposed within the handpiece housing; and
wherein the system further comprises a cable providing the electronic communication between the image sensor and the processor.

7. The system of claim 4, further comprising a light source disposed within the handpiece housing.

8. The system of claim 1, further comprising a light source and a fiber optic cable, wherein the fiber optic cable carries electromagnetic radiation from the light source to a distal end of the scope tip.

9. The system of claim 1, wherein the processor comprises one or more single-board computers.

10. The system of claim 1, wherein the instructions further comprise compressing the image and packaging the image within a data packet to be transmitted over the Internet to the remote server.

11. The system of claim 1, wherein the instructions further comprise adjusting one or more of white balance, exposure, or gain on the image prior to providing the image to the remote server by way of the network connection.

12. The system of claim 1, further comprising:
a housing, wherein the processor is disposed within an interior space defined by the housing;
a handpiece housing configured to be held by a user; and
a scope tip removably attached to the handpiece housing;
wherein the handpiece housing and the scope tip are external to the housing comprising the processor.

13. The system of claim 1, further comprising a flexible tube configured to be inserted into one or more of a nasal passageway or a throat of a user, and wherein the image sensor is disposed at a distal end or a proximal end of the flexible tube.

14. The system of claim 13, further comprising a fiber optic cable disposed within the flexible tube configured to carry electromagnetic radiation from a light source to the distal end of the flexible tube.

15. The system of claim 1, further comprising:
a handpiece housing configured to be held by a user;
a removable scope tip attached to the handpiece housing, wherein the removable scope tip is configured to enable visualization of one or more of an external auditory canal of a user, a nasal passageway of the user, or a throat of the user;
the image sensor disposed within the handpiece housing; and
the processor disposed within the handpiece housing.

16. The system of claim 1, further comprising the remote server in communication with the first computing device and the second computing device, wherein the remote server is configured to execute instructions stored in non-transitory computer readable storage medium, the instructions comprising:
establishing a network connection between the first computing device and the second computing device;
receiving a video stream captured by the image sensor of the scope;
providing the video stream to each of the first computing device and the second computing device in real-time.

17. The system of claim 16, wherein the instructions are such that establishing the network connection between the first computing device and the second computing device comprises establishing one or more of a video conference or an audio conference via a cloud-based conferencing system.

18. The system of claim 16, wherein the instructions further comprise:
rendering a user interface for a medical teleconferencing platform, wherein the medical teleconferencing platform enables a first user associated with the first computing device to join an audiovisual conference with a second user associated with the second computing device;
wherein the first user captures the video stream with the image sensor of the scope in real-time while communicating with the second user of the medical teleconferencing platform.

19. The system of claim 16, wherein the instructions further comprise:
encrypting a recording of the video stream;
storing the recording of the video stream on a cloud-based storage resource; and
applying permissions to the cloud-based storage resource such that only authorized persons may read or write to the recording of the video stream.

20. The system of claim 1, further comprising one or more network antennas, wherein the one or more network antennas enable:
the processor to communicate with the remote server by way of a wireless or wired Internet connection; and
the processor to communicate with a mobile device by way of a Bluetooth® connection.

* * * * *